(12) United States Patent
Breitenbucher et al.

(10) Patent No.: US 6,489,337 B1
(45) Date of Patent: Dec. 3, 2002

(54) METHOD FOR TREATING HISTAMINE $H_3$ RECEPTOR-MEDIATED DISORDERS WITH 2- OR 3-ARYL SUBSTITUTED IMIDAZO[1,2-A] PYRIDINES

(75) Inventors: J. Guy Breitenbucher, Escondido, CA (US); Nicholas I. Carruthers, Poway, CA (US); Xiaobing Li, Flemington, NJ (US); Timothy W. Lovenberg, San Diego, CA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 0 days.

(21) Appl. No.: 09/820,418

(22) Filed: Mar. 29, 2001

Related U.S. Application Data

(60) Provisional application No. 60/194,071, filed on Mar. 31, 2000, and provisional application No. 60/272,290, filed on Feb. 28, 2001.

(51) Int. Cl.[7] ............................................... A61K 31/44
(52) U.S. Cl. ....................................................... 514/300
(58) Field of Search ......................................... 514/300

(56) References Cited

U.S. PATENT DOCUMENTS

| | | |
|---|---|---|
| 4,727,145 A | 2/1988 | Press |
| 4,833,149 A | 5/1989 | Press |
| 4,880,824 A | 11/1989 | Press et al. |
| 5,182,291 A | 1/1993 | Gubin et al. |

FOREIGN PATENT DOCUMENTS

| | | |
|---|---|---|
| EP | 0 289 371 A1 | 11/1988 |
| EP | 0 978 512 A1 | 2/2000 |
| JP | 52 113992 A | 9/1977 |
| WO | 01/74815 A2 | 10/2001 |

OTHER PUBLICATIONS

Pauline J. Sanfilippo, Maud Urbanski, Jeffery B. Press; Hajos G.. Zoltan, David A. Shriver, Cynthia K. Scott "Synthesis of (Aryloxy)alkylamines. 1. Novel Antisecretory Agents with H+ K+ –ATPase Inhibitory Activity", Journal of Medicinal Chemistry, 1988, pp. 1778–1785, vol. 31.

Pauline J. Sanfilippo, Maud Urbanski, Jeffery B. Press, Barry Dubinsky and John B. Moore, Jr., "Synthesis of (Aryloxy)alkylamines. 2. Novel Imidazo–fused Heterocycles with Calcium Channel Blocking and Local Anesthetic Activity", Journal of Medicinal Chemistry, 1988, pp. 2221–2227, vol. 31.

PCT International Search Report dated Jan. 9, 2002 of International Application No. PCT/US01/10319.

*Primary Examiner*—William R. A. Jarvis

(57) ABSTRACT

The invention features methods of using pharmaceutically-active 2- or 3-aryl substituted imidazopyridines for the treatment of histamine $H_3$ receptor-mediated disorders.

26 Claims, No Drawings

METHOD FOR TREATING HISTAMINE H₃ RECEPTOR-MEDIATED DISORDERS WITH 2- OR 3-ARYL SUBSTITUTED IMIDAZO[1,2-A] PYRIDINES

CROSS-REFERENCE TO RELATED APPLICATIONS

This application claims priority from U.S. Provisional Application Ser. No. 60/194,071, filed on Mar. 31, 2000, and U.S. Provisional Application Ser. No. 60/272,290, filed on Feb. 28, 2001.

FIELD OF THE INVENTION

The invention relates to methods of using pharmaceutically-active fused heterobicyclic compounds to treat or prevent disorders and conditions mediated by the histamine $H_3$ receptor.

BACKGROUND

The histamine $H_3$ receptor is located as a presynaptic autoreceptor in the central nervous system and as a presynaptic heteroreceptor on serotonergic, noradrenergic, dopaminergic, and cholinergic neurons. The histamine $H_3$ receptor is also located peripherally in tissues such as vascular smooth muscle cells.

Proposed uses of histamine $H_3$ antagonists include the treatment or prevention of dementia, Alzheimer's disease (Panula et al. *Abstr. Society Neuroscience*, 1995, 21:1977), epilepsy (Yokoyama et al. *Eur. J. Pharmacol.*, 1993, 234:129), sleep/wake disorders (Lin et al, *Br. Res.*, 1990, 523, 325; Monti et al., *Eur. J. Pharmacol.*, 1991, 205, 283) including narcolepsy, insomnia, and jet lag, eating disorders (Machidori et al. *Brain Research*, 1992, 590:180), motion sickness, vertigo, attention deficit hyperactivity disorder, learning and memory disorders (Barnes et al. *Abstr. Society Neuroscience*, 1993,19:1813), schizophrenia (Schlicker et al. *Naunyn Schmiedeberg's Arch. Pharmacol.*, 1996, 353:325), and sequelae associated with post-ischemic reperfusion and hypertension (Imamura et al., *J. Pharmacol. Expt. Ther.*, 1994, 271, 1259). $H_3$ antagonists are also useful to treat or prevent neurogenic inflammation such as migraine (McLeod et al., *Abstr. Society Neuroscience*, 1996, 22, 2010), asthma (Ichinose et al, *Eur. J. Pharmacol.*, 989, 174, 49), obesity, allergic rhinitis, substance abuse, bipolar disorders, manic disorders, and depression. Histamine $H_3$ antagonists alone or in combination with a histamine $H_1$ antagonist are believed to be useful in the treatment of upper airway allergic response or allergic rhinitis (see, e.g., U.S. Pat. Nos. 5,217,986, 5,352,707, and 5,869,479).

As noted, the prior art related to histamine $H_3$ ligands was comprehensively reviewed recently ("*The Histamine $H_3$ Receptor-A Target for New Drugs*", Leurs, R., and Timmerman, H., (Editors), Elsevier, 1998). Within this reference the medicinal chemistry of histamine $H_3$ agonists and antagonists was reviewed (see Krause et al. and Phillips et al., respectively). Thus the importance of an imidazole moiety containing only a single substitution in the 4 position was noted together with the deleterious effects of additional substitution on activity. Particularly methylation of the imidazole ring at any of the remaining unsubstituted positions was reported to strongly decrease activity.

More recently several publications have described histamine $H_3$ ligands that do not contain an imidazole moiety. Examples include Ganellin et al *Arch. Pharm.* (Weinheim, Ger.) 1998, 331, 395; Walczynski et al *Arch. Pharm.* (Weinheim,Ger.) 1999, 332, 389; Walczynski et al *Farmaco* 1999, 684; Linney et al *J. Med. Chem.* 2000, 2362; U.S. Pat. No. 5,352,707; PCT Application WO99/42458, published Aug. 26,1999; and European Patent Application 0978512, published on Feb. 9, 2000.

SUMMARY OF THE INVENTION

The invention features the use of the compounds of formula (I) for the treatment and/or prevention of diseases and conditions mediated by the histamine 3 ($H_3$) receptor.

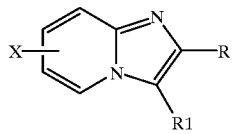

(I)

wherein
X is H or one or more of halogen, hydroxy, $C_{1-3}$alkoxy, benzyloxy, and $C_{1-6}$ alkyl;
R is H or Ar;
$R_1$ is H, methyl, or Ar;
Ar is $-(C=O)_n-Ph-O-(CH_2)_m-N(R_2)_2$;
$R_2$ is $C_{1-6}$ alkyl;
n is 0 or 1 when R is Ar or 1 when $R_1$ is Ar;
m is 2–6;
at least one of R and $R_1$ is Ar; and both of R and $R_1$ are not Ar;
or a pharmaceutically acceptable salt, ester, or amide thereof.

The compounds are disclosed generically in U.S. Pat. No. 4,727,145, and JP Serial Number 236427, filed on Sep. 22, 1987 and subsequently published as JP 63091391 A2. These compounds were first identified as having local anesthetic properties.

Additional features of the invention are disclosed in the following description and examples, and in the appended claims.

DETAILED DESCRIPTION

The invention features pharmaceutically active phenyl-substituted imidazopyridines and methods of making and using them. The description is organized as follows:
A. Terms
B. Compounds
C. Synthetic Methods
D. Uses
E. Synthetic Chemical Examples
F. Biological Examples
G. Other Embodiments
H. Claims A. Terms The following terms are defined below and by their usage throughout this disclosure.

"Alkyl" includes straight chain and branched hydrocarbons with at least one hydrogen removed to form a radical group. Alkyl groups include methyl, ethyl, propyl, isopropyl, butyl, isobutyl, t-butyl, 1-methylpropyl, pentyl, isopentyl, sec-pentyl, hexyl, heptyl, octyl, and so on.

"Alkoxy" includes a straight chain or branched alkyl group with a terminal oxygen linking the alkyl group to the rest of the molecule. Alkoxy includes methoxy, ethoxy, propoxy, isopropoxy, butoxy, t-butoxy, pentoxy and so on.

"halo" or "halogen" includes fluoro, chloro, bromo, and iodo, and preferably fluoro or chloro.

"patient" or "subject" includes mammals such as humans and animals (dogs, cats, horses, rats, rabbits, mice, non-human primates) in need of observation, experiment, treatment or prevention in connection with the relevant disease or condition. Preferably, the patient is a human.

"composition" includes a product comprising the specified ingredients in the specified amounts as well as any product which results directly or indirectly from combinations of the specified ingredients in the specified amounts.

Concerning the various radicals in this disclosure and in the claims, two general remarks are made. The first remark concerns valency. As with all hydrocarbon radicals, whether saturated, unsaturated or aromatic, and whether or not cyclic, straight chain, or branched, and also similarly with all heterocyclic radicals, each radical includes substituted radicals of that type and monovalent, bivalent, and multivalent radicals as indicated by the context of the claims. The context will indicate that the substituent is an alkylene or hydrocarbon radical with at least two hydrogen atoms removed (bivalent) or more hydrogen atoms removed (multivalent).

Second, radicals or structure fragments as defined herein are understood to include substituted radicals or structure fragments. Using "alkyl" as an example, "alkyl" should be understood to include substituted alkyl having one or more substitutions, such as between 1 and 5, 1 and 3, or 2 and 4 substituents. The substituents may be the same (dihydroxy, dimethyl), similar (chlorofluoro), or different (chlorobenzyl- or aminomethyl-substituted). Examples of substituted alkyl include haloalkyl (such as fluoromethyl, chloromethyl, difluoromethyl, perchloromethyl, 2-bromoethyl, and 3-iodocyclopentyl), hydroxyalkyl, aminoalkyl, nitroalkyl, alkylalkyl, and so on.

B. Compounds

One aspect of the invention features compounds of formula (I) as described in the Summary section above.

Preferred compounds of formula (I) include those compounds wherein: (a) each X is independently selected from H and methyl; (b) $R_1$ is H or methyl; (c) R is Ar; (d) $R_2$ is methyl, ethyl, propyl, isopropyl, butyl, isobutyl, sec-butyl, pentyl, isopentyl, sec-pentyl, tert-pentyl; (e) $R_2$ is methyl, ethyl, propyl, isopropyl, butyl, or pentyl; (f) n is 1; (g) n is 0; (h) m is 2, 3, or 4; (i) m is 3 or 4; (j) m is 3; or (k) combinations thereof.

More preferred compounds include those wherein X is H or methyl; R is Ar; $R_1$ is H or methyl; m is 2, 3, or 4; and n is 0. In one aspect, there is a single X as methyl; in another aspect, there is more than one X that is methyl, a halogen, or hydroxy.

Preferred compounds include: 2-(4-dibutylaminopropoxyphenyl)imidazo[1,2-a]pyridine; 2-(4-dibutylaminopropoxyphenyl)-8-methylimidazo[1,2-a]pyridine; 2-(4-dibutylaminopropoxyphenyl)-6-bromoimidazo[1,2-a]-pyridine; 2-(4-dibutylaminopropoxyphenyl)-7-methylimidazo-[1,2-a]pyridine; 2-(4-dibutylaminopropoxyphenyl)-3,8-dimethyl imidazo[1,2-a]pyridine; 2-(4-dibutylaminopropoxyphenyl)-8-hydroxyimidazo[1,2-a]pyridine; and 2-(4-dibutylaminopropoxyphenyl)-8-benzoyloxyimidazo[1,2-a]pyridine.

Preferred compounds also include: 2-(4-dibutylaminopropoxybenzoyl)-8-methylimidazo[1,2-a]-pyridine; 2-(4-dibutylaminopropoxybenzoyl)-5,7-dimethylimidazo[1,2-a]pyridine; 2-(4-dibutylaminopropoxybenzoyl)-7-methylimidazo[1,2-a] pyridine; 2-(4-dibutylaminopropoxybenzoyl)-8-benzyloxyimidazo[1,2-a]pyridine; and 2-(4-dibutylaminopropoxybenzoyl)-6-bromoimidazo[1,2-a] pyridine.

Additional preferred compounds include: 3-(4-dibutylaminopropoxybenzoyl)-8-methylimidazo[1,2-a]-pyridine and 3-(4-dibutylaminopropoxybenzoyl)-6-bromoimidazo[1,2-a]pyridine.

Other examples of compounds, and methods of making them, are provided in the examples below.

C. Synthetic Methods

The invention provides methods of making the disclosed compounds according to traditional organic synthetic methods as well as matrix or combinatorial synthetic methods. Traditional organic synthetic methods are described in U.S. Pat. No. 4,727,145, which is incorporated by reference in its entirety. Further guidance is found in Chemical Examples 1–15 below.

D. Uses

According to the invention, the disclosed compounds and compositions are useful for the amelioration of symptoms associated with, the treatment of, and/or the prevention of, the following conditions and diseases, or symptoms associated with them: dementia, Alzheimer's disease, narcolepsy, eating disorders, motion sickness, vertigo, attention deficit hyperactivity disorder, learning and memory disorders, schizophrenia, mild cognitive impairment, upper airway allergic response (allergic rhinitis), insomnia, jet lag, obesity, asthma, neurogenic inflammation, substance abuse, bipolar disorders, manic disorders, and depression. The invention also features pharmaceutical compositions, which include, without limitation, one or more of the disclosed compounds, and a pharmaceutically acceptable carrier or excipient.

1. Dosages

Those skilled in the art will be able to determine, according to known methods, the appropriate dosage for a patient, taking into account factors such as age, weight, general health, the type of symptoms requiring treatment, and the use of other medications. An effective amount means that amount of pharmaceutical reagent (such as a prodrug, metabolic precursor, or active compound) that elicits the biological or medical response desired. In general, a therapeutically effective amount will be between 0.01 and 1000 mg/kg per day, preferably between 0.01 and 250 mg/kg body weight, and daily dosages will be between 0.50 and 5000 mg for an adult subject of normal weight. Capsules, tablets or other formulations (such as liquids and film-coated tablets) may be of between 0.20 and 100 mg, such as 0.20, 0.50, 1, 2, 3, and 10 mg can be administered according to the disclosed methods.

2. Formulations

Dosage unit forms include tablets, capsules, pills, powders, granules, aqueous and nonaqueous oral solutions and suspensions, and parenteral solutions packaged in containers adapted for subdivision into individual doses. Dosage unit forms can also be adapted for various methods of administration, including controlled release formulations, such as subcutaneous implants. Administration methods include oral, rectal, parenteral (intravenous, intramuscular, subcutaneous), intracisternal, intravaginal, intraperitoneal, intravesical, local (drops, powders, ointments, gels or cream), and by inhalation (a buccal or nasal spray) as appropriate depending on the overall health and condition of the patient as determined by a physician or veterinary doctor.

Parenteral formulations include pharmaceutically acceptable aqueous or nonaqueous solutions, dispersion, suspensions, emulsions, and sterile powders for the preparation thereof. Examples of carriers include water, ethanol, polyols (propylene glycol, polyethylene glycol), vegetable oils, and injectable organic esters such as ethyl oleate. Fluidity can be maintained by the use of a coating such as lecithin, a surfactant, or maintaining appropriate particle size. Carriers for solid dosage forms include (a) fillers or extenders, (b) binders, (c) humectants, (d) disintegrating agents, (e) solution retarders, (f) absorption accelerators, (g) adsorbants, (h) lubricants, (i) buffering agents, and (j)propellants.

Compositions may also contain adjuvants such as preserving, wetting, emulsifying, and dispensing agents; antimicrobial agents such as parabens, chlorobutanol, phenol, and sorbic acid; isotonic agents such as a sugar or sodium chloride; absorption-prolonging agents such as aluminum monostearate and gelatin;.and absorption-enhancing agents.

3. Combination Therapy

The present invention also provides compositions and methods useful for the treatment of disorders or conditions modulated, preferably antagonized, by the histamine $H_3$ receptor in combination with compounds that modulate other receptors including, but not limited to, histamine $H_1$ and histamine $H_2$ receptors. The present invention includes compounds and compositions useful in methods of combination therapy for the treatment of diseases or conditions modulated by the histamine $H_3$ receptor in combination with compounds that are selective serotonin re-uptake inhibitors (SSRIs), such as PROZAC™, or are selective norepinephrine uptake inhibitors. Such combination methods include (a) administering the two or more pharmaceutical agents separately formulated and at separate times, and (b) administering the two or more agents simultaneously in a single formulation or in separate formulations administered more or less at the same time. For example, one aspect is a method of treatment comprising administering at least one histamine $H_3$ receptor modulating compound disclosed herein and administering at least one compound selected from a histamine $H_1$ receptor modulating compound, a histamine $H_2$ receptor modulating compound, a selective serotonin reuptake inhibitor (such as PROZAC™), or a selective norepinephrine uptake inhibiting compound.

4. Related Compounds

The invention provides the disclosed compounds and closely related, pharmaceutically acceptable forms of the disclosed compounds, such as salts, esters, amides, acids, hydrates or solvated forms thereof; masked or protected forms; and racemic mixtures, or enantiomerically or optically pure forms.

Pharmaceutically acceptable salts, esters, and amides include carboxylate salts (e.g., $C_{1-8}$alkyl, cycloalkyl, aryl, heteroaryl, or non-aromatic heterocyclic) amino acid addition salts, esters, and amides which are within a reasonable benefit/risk ratio, pharmacologically effective and suitable for contact with the tissues of patients without undue toxicity, irritation, or allergic response. Representative salts include hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, and laurylsulfonate. These may include alkali metal and alkali earth cations such as sodium, potassium, calcium, and magnesium, as well as non-toxic ammonium, quaternary ammonium, and amine cations such as tetramethyl ammonium, methylamine, trimethylamine, and ethylamine. See example, S. M. Berge, et al., "Pharmaceutical Salts," *J. Pharm. Sci.*, 1977, 66:1–19 which is incorporated herein by reference. Representative pharmaceutically acceptable amides of the invention include those derived from ammonia, primary $C_{1-6}$ alkyl amines and secondary di($C_{1-6}$ alkyl)amines. Secondary amines include 5- or 6-membered heterocyclic or heteroaromatic ring moieties containing at least one nitrogen atom and optionally between 1 and 2 additional heteroatoms. Preferred amides are derived from ammonia, $C_{1-3}$ alkyl primary amines, and di ($C_{1-2}$ alkyl)amines. Representative pharmaceutically acceptable esters of the invention include $C_{1-7}$ alkyl, $C_{5-7}$ cycloalkyl, phenyl, and phenyl($C_{1-6}$)alkyl esters. Preferred esters include methyl esters.

The invention also includes disclosed compounds having one or more functional groups (e.g., hydroxyl, amino, or carboxyl) masked by a protecting group. See, e.g., Greene and Wuts, *Protective Groups in Organic Synthesis*, 3$^{rd}$ ed., (1999) John Wiley & Sons, NY. Some of these masked or protected compounds are pharmaceutically acceptable; others will be useful as intermediates. Synthetic intermediates and processes disclosed herein, and minor modifications thereof, are also within the scope of the invention.

Hydroxyl Protecting Groups

Protection for the hydroxyl group includes methyl ethers, substituted methyl ethers, substituted ethyl ethers, substitute benzyl ethers, and silyl ethers.

Substituted Methyl Ethers

Examples of substituted methyl ethers include methoxymethyl, methylthiomethyl, t-butylthiomethyl, (phenyldimethylsilyl)methoxymethyl, benzyloxymethyl, p-methoxybenzyloxymethyl, (4-methoxyphenoxy)methyl, guaiacolmethyl, t-butoxymethyl, 4-pentenyloxymethyl, siloxymethyl, 2-methoxyethoxymethyl, 2,2,2-trichloroethoxymethyl, bis(2-chloroethoxy)methyl, 2-(trimethylsilyl)ethoxymethyl, tetrahydropyranyl, 3-bromotetrahydropyranyl, tetrahydrothiopyranyl, 1-methoxycyclohexyl, 4-methoxytetrahydropyranyl, 4-methoxytetrahydrothiopyranyl, 4-methoxytetrahydrothiopyranyl S,S-dioxido, 1-[(2-chloro-4-methyl)phenyl]-4-methoxypiperidin-4-yl, 1,4-dioxan-2-yl, tetrahydrofuranyl, tetrahydrothiofuranyl and 2,3,3a,4,5,6,7,7a-octahydro-7,8,8-trimethyl-4,7-methanobenzofuran-2-yl.

Substituted Ethyl Ethers

Examples of substituted ethyl ethers include 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, and benzyl.

Substituted Benzyl Ethers

Examples of substituted benzyl ethers include p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2- and 4-picolyl, 3-methyl-2-picolyl N-oxide, diphenylmethyl, p, p'-dinitrobenzhydryl, 5-dibenzosuberyl, triphenylmethyl, α-naphthyidiphenylmethyl, p-methoxyphenyidiphenylmethyl, di(p-methoxyphenyl) phenylmethyl, tri(p-methoxyphenyl)methyl, 4-(4'-bromophenacyloxy)phenyldiphenylmethyl, 4,4',4"-tris(4,5-dichlorophthalimidophenyl)methyl, 4,4',4'-tris (levulinoyloxyphenyl)methyl, 4,4',4"-tris (benzoyloxyphenyl)methyl, 3-(Imidazol-1-ylmethyl)bis(4', 4"-dimethoxyphenyl)methyl, 1,1-bis(4-methoxyphenyl)-1'-pyrenylmethyl, 9-anthryl, 9-(9-phenyl)xanthenyl, 9-(9- phenyl-10-oxo)anthryl, 1,3-benzodithiolan-2-yl, and benzisothiazolyl S,S-dioxido.

Silyl Ethers

Examples of silyl ethers include trimethylsilyl, triethylsilyl, triisopropylsilyl, dimethylisopropylsilyl, diethylisopropylsilyl, dimethylthexylsilyl, t-butyldimethylsilyl, t-butyldiphenylsilyl, tribenzylsilyl, tri-p-xylylsilyl, triphenylsilyl, diphenylmethylsilyl, and t-butylmethoxyphenylsilyl.

Esters

In addition to ethers, a hydroxyl group may be protected as an ester. Examples of esters include formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, p-P-phenylacetate, 3-phenylpropionate, 4-oxopentanoate(levulinate), 4,4-(ethylenedithio)pentanoate, pivaloate, adamantoate, crotonate, 4-methoxycrotonate, benzoate, p-phenylbenzoate, 2,4,6-trimethylbenzoate(mesitoate)

Carbonates

Examples of carbonate protecting groups include methyl, 9-fluorenylmethyl, ethyl, 2,2,2-trichloroethyl, 2-(trimethylsilyl)ethyl, 2-(phenylsulfonyl)ethyl, 2-(triphenylphosphonio)ethyl, isobutyl, vinyl, allyl, p-nitrophenyl, benzyl, p-methoxybenzyl, 3,4-dimethoxybenzyl, o-nitrobenzyl, p-nitrobenzyl, S-benzyl thiocarbonate, 4-ethoxy-1-naphthyl, and methyl dithiocarbonate.

Assisted Cleavage

Examples of assisted cleavage include 2-iodobenzoate, 4-azidobutyrate, 4-nitro-4-methylpentanoate, o-(dibromomethyl)benzoate, 2-formylbenzenesulfonate, 2-(methylthiomethoxy)ethyl carbonate, 4-(methylthiomethoxy)butyrate, and 2-(methylthiomethoxymethyl)benzoate.

Miscellaneous Esters

Examples of miscellaneous esters include 2,6-dichloro-4-methylphenoxyacetate, 2,6-dichloro4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate (tigloate), o-(methoxycarbonyl)benzoate, p-P-benzoate, α-naphthoate, nitrate, alkyl N,N,N',N'-tetramethylphosphorodiamidate, N-phenylcarbamate, borate, dimethylphosphinothioyl, and 2,4-dinitrophenylsulfenate

Sulfonates

Examples of sulfonates include sulfate, methanesulfonate (mesylate), benzylsulfonate, and tosylate.

Protection for 1.2- and 1.3-Diols

Cyclic Acetals and Ketals

Examples of cyclic acetals and ketals include methylene, ethylidene, 1-t-butylethylidene, 1-phenylethylidene, (4-methoxyphenyl)ethylidene, 2,2,2-trichloroethylidene, acetonide (isopropylidene), cyclopentylidene, cyclohexylidene, cycloheptylidene, benzylidene, p-methoxybenzylidene, 2,4-dimethoxybenzylidene, 3,4-dimethoxybenzylidene, and 2-nitrobenzylidene.

Cyclic Ortho Esters

Examples of cyclic ortho esters include methoxymethylene, ethoxymethylene, dimethoxymethylene, 1-methoxyethylidene, 1-ethoxyethylidine, 1,2-dimethoxyethylidene, α-methoxybenzylidene, 1-(N,N-dimethylamino)ethylidene derivative, α-(N,N-dimethylamino)benzylidene derivative, and 2-oxacyclopentylidene.

Silyl Derivatives

Examples of silyl derivatives include di-t-butylsilylene group, and 1,3-(1,1,3,3-tetraisopropyidisiloxanylidene) derivative.

Amino Protecting Groups

Protection for the amino group includes carbamates, amides, and special —NH protective groups.

Examples of carbamates include methyl and ethyl carbamates, substituted ethyl carbamates, assisted cleavage carbamates, photolytic cleavage carbamates, urea-type derivatives, and miscellaneous carbamates.

Carbamates

Examples of methyl and ethyl carbamates include methyl and ethyl, 9-fluorenylmethyl, 9-(2-sulfo)fluorenylmethyl, 9-(2,7-dibromo)fluorenylmethyl, 2,7-di-t-butyl-[9-(10,10-dioxo-10,10,10,10-tetrahydrothioxanthyl)]methyl, and 4-methoxyphenacyl.

Substituted Ethyl

Examples of substituted ethyl carbamates include 2,2,2-trichloroethyl, 2-trimethylsilylethyl, 2-phenylethyl, 1-(1-adamantyl)-1-methylethyl, 1,1-dimethyl-2-haloethyl, 1,1-dimethyl-2,2-dibromoethyl, 1,1-dimethyl-2,2,2-trichloroethyl, 1-methyl-1-(4-biphenylyl)ethyl, 1-(3,5-di-t-butylphenyl)-1-methylethyl, 2-(2'- and 4'-pyridyl)ethyl, 2-(N,N-dicyclohexylcarboxamido)ethyl, t-butyl, 1-adamantyl, vinyl, allyl, 1-isopropylallyl, cinnamyl, 4-nitrocinnamyl, 8-quinolyl, N-hydroxypiperidinyl, alkyldithio, benzyl, p-methoxybenzyl, p-nitrobenzyl, p-bromobenzyl, p-chlorobenzyl, 2,4-dichlorobenzyl, 4-methylsulfinylbenzyl, 9-anthrylmethyl and diphenylmethyl.

Assisted Cleavage

Examples of assisted cleavage include 2-methylthioethyl, 2-methylsulfonylethyl, 2-(p-toluenesulfonyl)ethyl, [2-(1,3-dithianyl)]methyl, 4-methylthiophenyl, 2,4-dimethylthiophenyl, 2-phosphonioethyl, 2-triphenylphosphonioisopropyl, 1,1-dimethyl-2-cyanoethyl, m-chloro-p-acyloxybenzyl, p-(dihydroxyboryl)benzyl, 5-benzisoxazolylmethyl, and 2-(trifluoromethyl)-6-chromonylmethyl.

Photolytic Cleavage

Examples of photolytic cleavage include m-nitrophenyl, 3,5-dimethoxybenzyl, o-nitrobenzyl, 3,4-dimethoxy-6-nitrobenzyl, and phenyl(o-nitrophenyl)methyl.

Urea-Type Derivatives

Examples of urea-type derivatives include phenothiazinyl-(10)-carbonyl derivative, N'-p-toluenesulfonylaminocarbonyl, and N'-phenylaminothiocarbonyl.

Miscellaneous Carbamates

Examples of miscellaneous carbamates include t-amyl, S-benzyl thiocarbamate, p-cyanobenzyl, cyclobutyl, cyclohexyl, cyclopentyl, cyclopropylmethyl, p-decyloxybenzyl, diisopropylmethyl, 2,2-dimethoxycarbonylvinyl, o-(N,N-dimethylcarboxamido)benzyl, 1,1-dimethyl-3-(N,N-dimethylcarboxamido)propyl, 1,1-dimethylpropynyl, di(2-pyridyl)methyl, 2-furanylmethyl, 2-iodoethyl, isobornyl, isobutyl, isonicotinyl, p-(p'-methoxyphenylazo)benzyl, 1-methylcyclobutyl, 1-methylcyclohexyl, 1-methyl-1-cyclopropylmethyl, 1-methyl-1-(3,5-dimethoxyphenyl)ethyl, 1-methyl-1-(p-phenylazophenyl)ethyl, 1-methyl-1-phenylethyl, 1-methyl-1-(4-pyridyl)ethyl, phenyl, p-(phenylazo)benzyl, 2,4,6-tri-t-butylphenyl, 4-(trimethylammonium)benzyl, and 2,4,6-trimethylbenzyl.

Examples of amides include:

Amides

N-formyl, N-acetyl, N-chloroacetyl, N-trichloroacetyl, N-trifluoroacetyl, N-phenylacetyl, N-3-phenylpropionyl, N-picolinoyl, N-3-pyridylcarboxamide, N-benzoylphenylalanyl derivative, N-benzoyl, N-p-phenylbenzoyl.

Assisted Cleavage

N-o-nitrophenylacetyl, N-o-nitrophenoxyacetyl, N-acetoacetyl, (N'-dithiobenzyloxycarbonylamino)acetyl, N-3-(p-hydroxyphenyl)propionyl, N-3-(o-nitrophenyl) propionyl, N-2-methyl-2-(o-nitrophenoxy)propionyl, N-2-methyl-2-(o-phenylazophenoxy)propionyl, N-4-chlorobutyryl, N-3-methyl-3-nitrobutyryl, N-o-nitrocinnamoyl, N-acetylmethionine derivative, N-o-nitrobenzoyl, N-o-(benzoyloxymethyl)benzoyl, and 4,5-diphenyl-3-oxazolin-2-one.

Cyclic Imide Derivatives

N-phthalimide, N-dithiasuccinoyl, N-2,3-diphenylmaleoyl, N-2,5-dimethylpyrrolyl, N-1,1,4,4-tetramethyldisilylazacyclopentane adduct, 5-substituted 1,3-dimethyl-1,3,5-triazacyclohexan-2-one, 5-substituted 1,3-dibenzyl-1,3,5-triazacyclohexan-2-one, and 1-substituted 3,5-dinitro-4-pyridonyl.

Special—NH Protective Groups

Examples of special NH protective groups include

N-Alkyl and N-Aryl Amines p N-methyl, N-allyl, N-[2-(trimethylsilyl)ethoxy]methyl, N-3-acetoxypropyl, N-(1-isopropyl-4-nitro-2-oxo-3-pyrrolin-3-yl), quaternary ammonium salts, N-benzyl, N-di(4-methoxyphenyl)methyl, N-5-dibenzosuberyl, N-triphenylmethyl, N-(4-methoxyphenyl) diphenylmethyl, N-9-phenylfluorenyl, N-2,7-dichloro-9-fluorenylmethylene, N-ferrocenylmethyl, and N-2-picolylamine N'-oxide.

Imine Derivatives

N-1,1-dimethylthiomethylene, N-benzylidene, N-p-methoxybenzylidene, N-diphenylmethylene, N-[(2-pyridyl) mesityl]methylene, and N-(N',N'-dimethylaminomethylene).

Protection for the Carbonyl Group

Acyclic Acetals and Ketals

Examples of acyclic acetals and ketals include dimethyl, bis(2,2,2-trichloroethyl), dibenzyl, bis(2-nitrobenzyl) and diacetyl.

Cyclic Acetals and Ketals

Examples of cyclic acetals and ketals include 1,3-dioxanes, 5-methylene-1,3-dioxane, 5,5-dibromo-1,3-dioxane, 5-(2-pyridyl)-1,3-dioxane, 1,3-dioxolanes, 4-bromomethyl-1,3-dioxolane, 4-(3-butenyl)-1,3-dioxolane, 4-phenyl-1,3-dioxolane, 4-(2-nitrophenyl)-1,3-dioxolane, 4,5-dimethoxymethyl-1,3-dioxolane, O,O'-phenylenedioxy and 1,5-dihydro-3H-2,4-benzodioxepin.

Acyclic Dithio Acetals and Ketals

Examples of acyclic dithio acetals and ketals include S,S'-dimethyl, S,S'-diethyl, S,S'-dipropyl, S,S'-dibutyl, S,S'-dipentyl, S,S'-diphenyl, S,S'-dibenzyl and S,S'-diacetyl.

Cyclic Dithio Acetals and Ketals

Examples of cyclic dithio acetals and ketals include 1,3-dithiane, 1,3-dithiolane and 1,5-dihydro-3H-2,4-benzodithiepin.

Acyclic Monothio Acetals and Ketals

Examples of acyclic monothio acetals and ketals include O-trimethylsilyl-S-alkyl, O-methyl-S-alkyl or -S-phenyl and O-methyl-S-2-(methylthio)ethyl.

Cyclic Monothio Acetals and Ketals

Examples of cyclic monothio acetals and ketals include 1,3-oxathiolanes.

Miscellaneous Derivatives

O-Substituted Cyanohydrins

Examples of O-substituted cyanohydrins include O-acetyl, O-trimethylsilyl, O-1-ethoxyethyl and O-tetrahydropyranyl.

Substituted Hydrazones

Examples of substituted hydrazones include N,N-dimethyl and 2,4-dinitrophenyl.

Oxime Derivatives

Examples of oxime derivatives include O-methyl, O-benzyl and O-phenylthiomethyl.

Imines

Substituted Methylene Derivatives, Cyclic Derivatives

Examples of substituted methylene and cyclic derivatives include oxazolidines, 1-methyl-2-(1'-hydroxyalkyl) imidazoles, N,N'-dimethylimidazolidines, 2,3-dihydro-1,3-benzothiazoles, diethylamine adducts, and methylaluminum bis(2,6-di-t-butyl-4-methylphenoxide)(MAD)complex.

Monoprotection of Dicarbonyl Compounds

Selective Protection of α- and β-Diketones

Examples of selective protection of α- and β-diketones include enamines, enol acetates, enol ethers, methyl, ethyl, i-butyl, piperidinyl, morpholinyl, 4-methyl-1,3-dioxolanyl, pyrrolidinyl, benzyl, S-butyl, and trimethylsilyl.

Cyclic Ketals, Monothio and Dithio Ketals

Examples of cyclic ketals, monothio and dithio ketals include bismethylenedioxy derivatives and tetramethylbis-methylenedioxy derivatives.

Protection for the Carboxyl Group

Esters

Examples of esters include the following.

Substituted Methyl Esters

Examples of substituted methyl esters include 9-fluorenylmethyl, methoxymethyl, methylthiomethyl, tetrahydropyranyl, tetrahydrofuranyl, methoxyethoxymethyl, 2-(trimethylsilyl)ethoxymethyl, benzyloxymethyl, phenacyl, p-bromophenacyl, α-methylphenacyl, p-methoxyphenacyl, carboxamidomethyl, and N-phthalimidomethyl.

2-Substituted Ethyl Esters

Examples of 2-substituted ethyl esters include 2,2,2-trichloroethyl, 2-haloethyl, ω-chloroalkyl, 2-(trimethylsilyl) ethyl, 2-methylthioethyl, 1,3-dithianyl-2-methyl, 2-(p-nitrophenylsulfenyl)ethyl, 2-(p-toluenesulfonyl)ethyl, 2-(2'-pyridyl)ethyl, 2-(diphenylphosphino)ethyl, 1-methyl-1-phenylethyl, t-butyl, cyclopentyl, cyclohexyl, allyl, 3-buten-1-yl, 4-(trimethylsilyl)-2-buten-1-yl, cinnamyl, α-methylcinnamyl, phenyl, p-(methylmercapto)phenyl and benzyl.

Substituted Benzyl Esters

Examples of substituted benzyl esters include triphenylmethyl, diphenylmethyl, bis(o-nitrophenyl)methyl, 9-anthrylmethyl, 2-(9,10-dioxo)anthrylmethyl, 5-dibenzosuberyl, 1-pyrenylmethyl, 2-(trifluoromethyl)-6-chromylmethyl, 2,4,6-trimethylbenzyl, p-bromobenzyl, o-nitrobenzyl, p-nitrobenzyl, p-methoxybenzyl, 2,6-dimethoxybenzyl, 4-(methylsulfinyl)benzyl, 4-sulfobenzyl, piperonyl, 4-picolyl and p-P-benzyl.

Silyl Esters

Examples of silyl esters include trimethylsilyl, triethylsilyl, t-butyldimethylsilyl, i-propyldimethylsilyl, phenyldimethylsilyl and di-t-butylmethylsilyl.

Activated Esters

Examples of activated esters include thiols.

Miscellaneous Derivatives

Examples of miscellaneous derivatives include oxazoles, 2-alkyl-1,3-oxazolines, 4-alkyl-5-oxo-1,3-oxazolidines, 5-alkyl-4-oxo-1,3-dioxolanes, ortho esters, phenyl group and pentaaminocobalt(III) complex.

Stannyl Esters

Examples of stannyl esters include triethylstannyl and tri-n-butylstannyl.

Amides and Hydrazides

Amides

Examples of amides include N,N-dimethyl, pyrrolidinyl, piperidinyl, 5,6-dihydrophenanthridinyl, o-nitroanilides, N-7-nitroindolyl, N-8-Nitro-1,2,3,4-tetrahydroquinolyl, and p-P-benzenesulfonamides.

Hydrazides

Examples of hydrazides include N-phenyl and N,N'-diisopropyl hydrazides.

E. Synthetic Chemical Examples

Additional experimental descriptions of the compounds of the invention are found in the Examples of U.S. Pat. No. 4,727,145, incorporated herein by reference in its entirety. Examples 1–6 below correspond to Examples 1, 2, 13, 7, 8, and 14 of the '145 patent, respectively, and are provided as general guidance. A Japanese translation corresponding to the '145 patent may be found in JP Serial Number 236427, filed on Sep. 22, 1987 and subsequently published as JP 63091391 A2.

EXAMPLE 1

2-(4-Dibutylaminopropoxyphenyl)imidazo[1,2-a]pyridine

To a mixture of p-hydroxyacetophenone (50.7 g, 0.37 mol) and 1-bromo-3-chloropropane (160 ml, 1.5 mol) in methanol (250 mL) was added portionwise potassium hydroxide (63 g, 1.12 mol). The mixture was stirred at reflux for 24 hours, cooled to room temperature, filtered through Celite and evaporated in vacuo. The residual semi-solid was diluted with diethyl ether (500 ml) and washed with $H_2O$ (2×300 mL). The ether solution was dried over $MgSO_4$, filtered and evaporated in vacuo to give p-chloropropoxy acetophenone as a liquid in 68% yield (53.38 g). $^1$H NMR ($CDCl_3$): δ7.98–7.89 (d, J=8.9 Hz, 2H), 7.02–6.92 (d, J=8.9 Hz, 2H), 4.16 (t, J=5.9 Hz, 2H), 3.75 (t, J=6.4 Hz, 2H), 2.52 (s, 3H), 2.34–2.16 (m, 2H).

To a stirred solution of p-chloropropoxyacetophenone (53.3 g, 0.25 mol) in diethyl ether (250 mL) was slowly added bromine (13 ml, 0.25 mol) and allowed to stir at room temperature for 16 hours. The dark mixture was poured into an aqueous saturated sodium bicarbonate solution (300 mL) and the organic layer separated. The ether layer was washed with an aqueous saturated sodium bicarbonate solution (300 mL) and with water (300 mL) and dried over $MgSO_4$. The solution was filtered and evaporated in vacuo to yield α-bromo-4-chloropropoxy acetophenone (64.4 g, 88% yield) as a dark oil. $^1$H NMR ($CDCl_3$): δ7.96 (d, J=8.9 Hz, 2H), 6.95 (d, J=8.9 Hz, 2H), 4.41 (s, 2H), 4.19 (t, 2H), 3.75 (t, 2H), 2.26 (m, 2H).

A mixture of α-bromo-4-chloropropoxy acetophenone (12.8 g, 44 mmol) and 2-aminopyridine (4.0 g, 44 mmol) in ethanol (80 ml) was stirred at reflux for 3 hours, cooled at room temperature and filtered to give 2-(4-chloropropoxy-phenyl)imidazo[1,2-a]pyridine (5.2 g, 32% yield) as a white solid. $^1$H NMR ($CD_3OD$): δ8.81 (d, J=6.7 Hz, 1H), 8.51 (s, 1H), 7.97–7.01 (m, 7H)4.19 (t, J=5.9 Hz, 2H), 3.79 (t, J=6.3 Hz, 2H), 2.25 (m, 2H).

A suspension of 2-(4-chloropropoxyphenyl)imidazo[1,2-a]-pyridine (5.2 g, 14 mmol) in dibutylamine (30 mL) was stirred at reflux for 5 hours. The excess dibutylamine was removed by distillation and the resulting oil was flash chromatographed (silica gel, 9:1 $CH_2Cl_2$: acetone) to give the free base of the title compound (5.1 g, 93% yield) as an oil. The HCl salt was prepared by dropwise addition of concentrated hydrochloric acid to a solution of the free base in methanol, concentrated and recrystallized from methanol acetone to yield 2-(4-dibutylaminopropoxyphenyl)imidazo [1,2-a]pyridine as a white crystalline solid, mp 179° C. to 183° C. IR(KBr): 3400, 2620, 1650,1620 $cm^{-1.}$ $^{MS:}$ 380 ($MH^+$). $^1$H NMR ($CD_3OD$): δ8.80 (d, J=8 Hz, 1H), 8.52 (s, 1H), 7.92–7.49 (m, 5H), 7.18 (d, J=8 Hz, 2H), 4.23 (t, J=4.6 Hz, 2H), 3.50–3.13 (m, 6H), 2.25 (m, 2H), 1.82–1.34 (m, 8H), 1.01 (m, 6H).

Theor. $C_{24}H_{33}N_3O_3HCl$: C, 58.95; H, 7.42; N, 8.59. Found: C, 59.25; H, 7.71; N, 9.03.

When in the above procedure, p-hydroxypropiophenone is employed as the starting material, 2-(4-dibutylaminopropoxy-phenyl)-3-methylimidazo[1,2-a] pyridine is obtained as the resultant product.

EXAMPLE 2

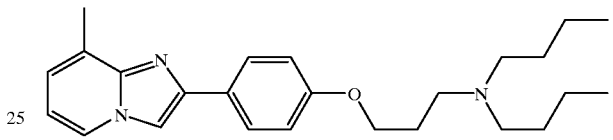

2-[4-[3-(Dibutylamino)propoxy]phenyl)-8-methylimidazo[1,2-a]pyridine $K_i$=500 nM The title compound was prepared as described in Example 1 above by reacting 3-methyl-2-aminopyridine (6.3 g, 15.8 mmol) with α-bromo-4-chloropropoxy-acetophenone. The product was reacted with dibutylamine as described above to produce (2.0 g, 32% yield) of the free base which was converted to the HCl salt, mp 214° C. to 217° C. IR(KBr): 3420, 2960, 1650, 1615 $cm^{-1}$. MS: 393 ($M^+$). $^1$HNMR ($CD_3OD$): 8.25 (d, J=6 Hz, 1H), 8.06 (s, 1H), 7.88 (d, J=7 Hz, 2H), 7.05 (m, 3H), 6.85 (t, J=6 Hz, 1H), 4.13 (t, J=4 Hz, 2H), 3.00–2.80 (m, 6H), 2.59 (s, 3H), 2.10 (m, 2H), 1.57–1.44 (m, 8H), 1.04 (m, 6H).

Theor. $C_{25}H_{35}N_3O_3HCl$: C, 59.70; H, 7.62; N, 8.35. Found: C, 59.61; H, 7.69; N, 8.37.

EXAMPLE 3

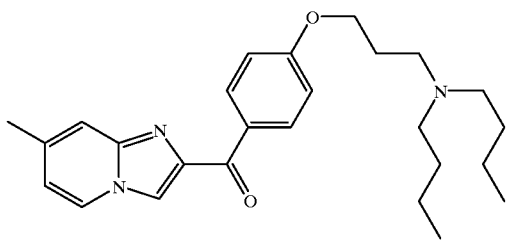

[4-(3-dibutylamino-propoxy)-phenyl]-(7-methyl-imidazo[1,2-a]pyridin-2-yl)-methanone $K_i$=70 nM This compound was prepared analogously to Example 2 above.

EXAMPLE 4

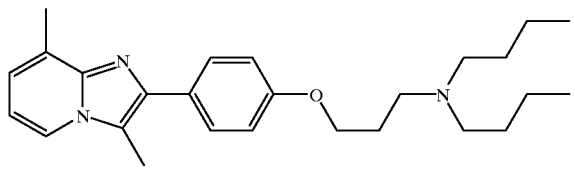

2-(4-Dibutylaminopropoxyphenyl)-3,8-dimethylimidazo[1,2-a]pyridine $K_i$=327 nM This compound was prepared according to the procedure described in Example 7 of U.S. Pat. No. 4,727,145, and provided below. p-Hydroxypropiophenone (50 g, 0.33 mmol) was reacted with 1-bromo-3-chloropropane and the resulting compound reacted with bromine as described in Example 1. The resulting compound was reacted with 3-methyl-2-aminopyridine (1.7 g, 16 mmol) and the product reacted with dibutylamine as described in Example 1 to produce 2.4 g. (62% yield) of the title compound as the HCl salt, mp 202° C.–204° C. IR(KBr): 3420, 2620, 1650 1605 cm$^{-1}$. MS: 408 (M$^+$). $^1$H NMR (CD$_3$OD): δ8.58 (d, J=6.5 Hz, 1H), 7.85–7.71 (m, 3H), 7.48 (t, J=6.7 Hz, 1H), 7.22 (d, J=8.7 Hz, 2H), 4.26 (t, J=5.8 Hz, 2H), 3.52–3.16 (m ,6H), 2.75 (s, 3H), 2.73 (s, 3H), 2.33 (m, 2H), 1.87–1.36 (m, 8H), 1.02 (m, 6H).

Theor. C$_{26}$H$_{37}$N$_3$O$_3$HCl.H$_2$O: C, 58.37; H, 7.91; N, 7.85. Found: C, 58.20; H, 7.98; N, 7.67.

When in the above procedure, 4,6-dimethyl-2-aminopyridine is used in place of 3-methyl-2-aminopyridine, 2-(4-dibutylaminopro-poxyphenyl)-3,5,7-trimethylimidazo[1,2-a]pyridine is obtained as the resultant product. Furthermore, when in any of the procedures disclosed herein, 1-bromo-2-chlorothane, 1-bromo-4-chlorobutane, or 1-bromo-5-chloropentane is used in place of 1-bromo-3-chloropropane, the corresponding 2-(4-dibutylaminoethoxyphenyl)-substituted imidazo[1,2-a]pyridines, 2-(4-dibutylaminobutoxyphenyl)-substituted imidazo[1,2-a]pyridines or 2-(4-dibutylaminopentoxyphenyl)-substituted imidazo[1,2-a]-pyridines are obtained.

When in any of the above procedures, dimethylamine, diethylamine, dipropylamine, dipentylamine or dihexylamine is used in place of dibutylamine, the corresponding 2-(4-dimethyl-, 2-(4-diethyl-, 2-(4-dipropyl-2-4(dipentyl- or 2-(4-dihexylaminopropoxyphenyl)-substituted imidazo[1,2-a]pyridines derivatives are obtained.

EXAMPLE 5

2-(4-Dibutylaminopropoxybenzoyl)-8-methylimidazo[1,2-a]pyridine $K_i$=500 nM This was prepared according to the procedure described in Example 8 of U.S. Pat. No. 4,727,145 and as provided below. To a solution of a α-bromoketone (60 g, 0.20 mol) in dimethylformamide (120 ml) was slowly added an aqueous solution of sodium hydroxide (8.6 g, 0.20 mol, in 50 ml of H$_2$O). The mixture was stirred at room temperature for 30 minutes, diluted with diethyl ether (500 ml) and washed once with H$_2$O (500 ml). The ether layer was dried over MgSO$_4$, filtered and concentrated to give α-hydroxy-(4-chloropropoxy)propiophenone (30.5 g, 65% yield) as a yellow oil. $^1$H NMR (CDCl$_3$): δ7.93 (d,J=8.9 Hz, 2H), 6.98 (d, J=8.9 Hz, 2H), 5.12 (m, 1H), 4.21 (t, J=5.9 Hz, 2H), 3.77 (t, J=6.2 Hz, 2H), 2.28 (m, 2H) 1.46 (d, J=6.9 Hz, 3H).

To a solution of α-hydroxy-(4-chloropropoxy)propiophenone (30.5 g, 0.13 mol) in methylene chloride (250 ml) was added pyridinium chlorochromate (41 g, 0.19 mol) portionwise. The mixture was stirred at room temperature for 24 hours, filtered through Celite and concentrated. The dark oil was taken up in diethyl ether, (500 ml) filtered again through Celite then concentrated to give α-keto-(4-chloropropoxy)propiophenone (18.7 g, 62% yield) as an amber oil. $^1$H NMR (CDCl$_3$): δ8.03 (d, J=8.9 Hz, 2H), 6.96 (d, J=8.9 Hz, 2H), 4.21 (t, J=5.9 Hz, 2H), 3.76 (t, J=6.2 Hz, 2H), 2.51 (s, 3H) 2.27 (m, 2H).

To a solution of α-keto-(4-chloropropoxy)propiophenone (18.7 g, 77.9 mmol) in diethyl ether (300 ml) was added bromine (4 ml, 77.9 mmol) dropwise. The solution was stirred at room temperature for 24 hours then poured into an aqueous saturated sodium bicarbonate solution (500 ml). The organic layer was separated, washed once again with an aqueous sodium bicarbonate solution, dried over MgSO$_4$, filtered and concentrated to give β-bromo-α-keto-(4-chloropropoxy)propiophenone (24.4 g, 98% yield) as an amber oil. $^1$H NMR (CDCl$_3$): δ8.02 (d, J=8.9 Hz, 2H), 6.99 (d, J=8.9 Hz, 2H), 4.40 (s, 2H), 4.23 (t, J=7.5 Hz, 2H), 3.76 (t, J=7.5 Hz, 2H) 2.70 (m, 2H).

A solution of 3-methyl-2-aminopyridine (1.6 g, 14.7 mmol) and β-bromo-αketo-(4-chloropropoxy)propiophenone (4.7 g, 14.7 mmol) in ethanol (50 ml) was stirred at reflux for 3 hours. The mixture was concentrated and the resulting semi-solid was recrystallized from methanol-acetone to give 2-(4-chloropropoxybenzoyl)-8-methylimidazo[1,2-a]pyridine as an off-white solid (2.4 g, 41% yield). $^1$HNMR (CDCl$_3$): δ9.94 (s, 1H), 9.59 (d, J=7.4 Hz, 1H), 8.21 (d, J=8.8 Hz, 2H), 7.73 (m, 1H), 7.10 (d, J=8.8 Hz, 2H) 6.74 (t, J=6.9 Hz, 1H), 4.25 (t, J=5.7 Hz, 2H), 3.77 (t, J=6.2 Hz, 2H), 2.76 (s, 3H), 2.30 (m, 2H).

A mixture of 2-(4-chloropropoxybenzoyl)-8-methylimidazo-[1,2-a]pyridine (2.4 g, 6.0 mmol) in dibutylamine (30 ml) was stirred at reflux for 8 hours. The excess dibutylamine was removed by distillation and the resulting oil was flash chromatographed (silica gel, acetone) to give the free base of the title compound (2.5 g, 100% yield) as a thick oil. The HCl salt was prepared by dropwise addition of concentrated hydrochloric acid to a solution of the title compound in methanol, concentrated and recrystallized from methanol-acetone, mp 159 to 161° C. IR(KBr): 3420, 1650 cm$^{-1}$. MS: 421 (M$^+$). $^1$HNMR (CD$_3$OD): δ8.89 (s, 1 H), 8.72 (d, J=6.6 Hz, 1H), 8.15 (d, J=8.9 Hz, 2H), 7.89 (d, J=7.3 Hz, 1H ), 7.48 (t, J=6.9 Hz, 1H ), 7.21 (d, J=8.9 Hz, 2H), 4.29 (t, J=7 Hz, 2H), 3.26 (m, 6H), 2.73 (s, 3H), 2.33 (m, 2H), 1.79–1.35 (m, 8H), 1.02 (m 6H).

EXAMPLE 6

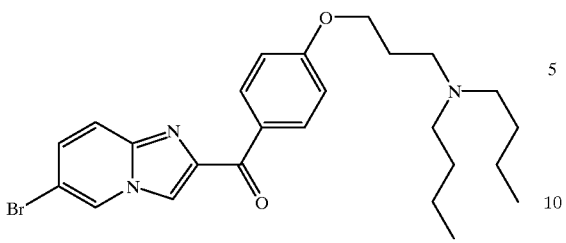

3-(4-Dibutylaminopropoxybenzoyl)-6-bromoimidazo[1,2-a]pyridine $K_i=1000$ nM

The title compound was prepared according to Example 5 above by utilizing 5-bromo-2-aminopyridine (5.0 g, 28.9 mmol) in place of the 3-methyl-2-aminopyridine to produce 4.5 g (60% yield) of the free base which was converted to the HCl salt, mp 214–216° C. IR(KBr): 3420, 2600, 2440, 1650, cm$^{-1}$. MS: 442 (M—C$_3$ H$_7^+$). 1HNMR (CD$_3$OD): δ9.20 (s, 1H), 8.86 (s, 1H), 8.21 (d, J=8.7 Hz, 2H), 8.07–7.80 (m, 2H), 7.17 (d, J=8.7 Hz, 2H), 4.5 (m, 2H), 4.5 (m, 2H), 1.78–1.25 (m, 8H), 0.95 (m, 6H).

When in the above procedure, 2-aminopyridine, 4-methyl-2-aminopyridine, 3-benzyloxy-2-aminopyridine, 4,6-dimethyl-2-aminopyridine, or 3-hydroxy-2-aminopyridine is used in the starting material, the corresponding 3-(4-dibutylaminopropoxybenzoyl)imidazo[1,2-a]pyridine, 3-(4-dibutylaminopropoxybenzoyl)-7-methylimidazo[1,2-a]pyridine, 3-(4-dibutylaminopropoxybenzoyl)-8-benzyloxyimidazo[1,2-a]pyridine, 3-(4-dibutylaminopropoxybenzoyl)-5,7-dimethylimidazo[1,2-a]pyridine, or 3-(4-dibutylaminopropoxybenzoyl)-8-hydroxyimidazo[1,2-a]pyridine is obtained.

When in any of the herein dibutylaminoethyl chloride, dimethylaminopentyl chloride, diethaminobutyl chloride or dipentylaminopropyl chloride is employed as the alkylating agent, the corresponding 3-(4-dibutylaminoethyoxy-, 3-(4-dimethylaminopentoxy-, 3-(4-diethylaminobutoxy-, or 3-(4-dipentylaminopropoxy- benzoyl)-substituted imidazo[1,2-a]pyridines are obtained.

EXAMPLE 7

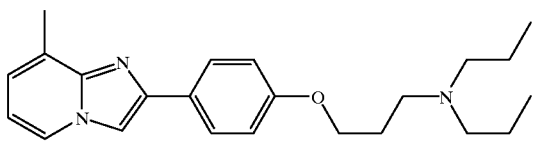

2-(4-Dipropylaminopropoxyphenyl)-8-methylimidazo[1,2-a]pyridine $K_i=44$ nM

This compound was prepared according to the procedure described in Example 1 above using 2-(4-chloropropoxyphenyl)-8-methylimidazo[1,2-a]pyridine and dipropylamine instead of 2-(4-chloropropoxyphenyl) imidazo[1,2-a]pyridine and dibutylamine respectively. Analysis Calc'd for C$_{23}$H$_{31}$N$_3$O 3HCl; C, 7.22; H, 58.16; N, 8.85. Found: C, 7.21; H, 58.66; N, 8.76.

EXAMPLE 8

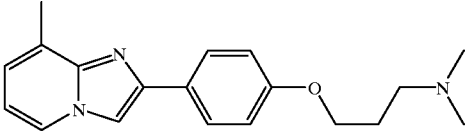

2-(4-Dimethylaminopropoxyphenyl)-8-methylimidazo[1,2-a]pyridine $K_i=14$ nM

This compound was prepared according to the procedure described in Example 1 above using 2-(4-chloropropoxyphenyl)-8-methylimidazo[1,2-a]pyridine and dimethylamine instead of 2-(4-chloropropoxyphenyl) imidazo[1,2-a]pyridine and dibutylamine respectively. 2-(4-Chloropropoxyphenyl)-8-methylimidazo[1,2-a]pyridine was prepared using 3-methyl-2-aminopyridine in stead of 2-aminopyridine. Analysis: Calc'd for C$_{19}$H$_{23}$N$_3$O 3HCl; C, 6.46; H, 52.24; N, 9.62. Found: C, 6.68; H, 52.38; N, 9.18.

EXAMPLE 9

2-(4-Dimethylaminopropoxyphenyl)imidazo[1,2-a]pyridine $K_i=119$ nM

The title compound was obtained (57 mg) by the same general method as that used to prepare 2-(4-(N-Ethyl)anilinoethoxyphenyl)imidazo[1,2-a]pyridine below, substituting 3-(N,N-dimethylamino)propanol for 2-(N-ethylanilino)ethanol. $^1$H NMR (CDCl$_3$) δ8.09 (d, 1H), 7.84 (d, 2H), 7.76 (s, 1H), 7.59 (d, 1H), 7.12 (dd, 1H), 6.96 (d, 2H), 6.72 (t, 1H), 4.04 (t, 2H), 2.48 (t, 2H), 2.26 (s, 6H), 1.97 (m, 2H); MS (ESI) m/z 295 (M+H).

Preparation of 2-(4-(N-Ethyl)anilinoethoxyphenyl)imidazo [1,2-a]pyridine

Step A Preparation of alpha-bromo-4-hydroxyacetophenone

Bromine (17.6 g, 110 mmol) was added dropwise to a 0° C. solution of 4-hydroxyacetophenone (15 g, 110 mmol) in ether (200 mL) over 20 minutes. The mixture was stirred for 1 hour and poured carefully into saturated sodium bicarbonate solution (500 mL). The organics were washed with saturated sodium bicarbonate solution, dried over magnesium sulfate and concentrated in vacuo. The crude product was then recrystallized from ether to afford the title compound (14.1 g).

Step B Preparation of 2-(4-hydroxyphenyl)-7-methylimidazo[1,2a]pyridinehydrobromide The product of Step A (430 mg, 2.0 mmol), and 2-picoline (188 mg, 2.0 mmol) were mixed in 2-propanol (4.0 mL) and stirred for 18 hr. The resulting crystals were collected and washed with 2-propanol and dried under vacuum to afford the title compound (287 mg).

Step C Preparation of 2-(4-(N-(ethyl)anilinoethoxy)phenyl) imidazo[1,2-a]pyridine A mixture of immobilized triphenylphisphine resin (300 mg, 0.9 meq (Fluka)), and the product of Step B (84 mg, 0.30 mmol) in tetrahydrofuran (2.5 mL) was treated with 2-(N-ethylanilino)ethanol (149 mg, 0.9 μmol) followed by diethyl azidodicarboxylate (142 uL, 0.9 mmol). The reaction was shaken for 20 hr. and filtered. The filtrate was concentrated in vacuo and the residue purified by silica gel chromatography (hexane/ethyl acetate) to afford the title compound (34 mg). MS (ESI): 358.

EXAMPLE 10

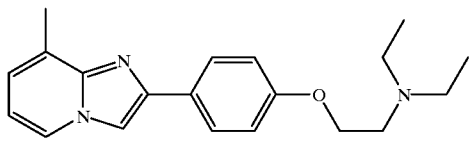

2-(4-Diethylaminoethoxyphenyl)-8-methylimidazo [1,2-a]pyridine $K_i$=15 nM

The title compound was prepared by condensing diethylamine with 2-(4-chloroethoxyphenyl)-8-methylimidazo[1,2-a]pyridine, the latter being prepared according to the procedure described in Example 1 above using 1-bromo-2-chloroethane in place of 1-bromo-3-chloropropane. Analysis Calc'd for $C_{20}H_{25}N_3O$ 3HCl; C, 6.52; H, 55.5; N, 9.71. Found: C, 6.84; H, 55.33; N, 9.54.

EXAMPLE 11

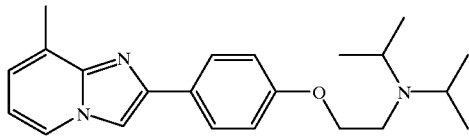

2-(4-Diisopropylaminoethoxyphenyl)-8-methylimidazo[1,2-a]pyridine $K_i$=55 nM

The title compound was prepared by condensing di-isopropylamine with 2-(4-chloroethoxyphenyl)-8-methylimidazo[1,2-a]pyridine. 2-(4-Chloroethoxyphenyl)-8-methylimidazo[1,2-1]pyridine was prepared according the procedure described in Example 1 above using 1-bromo-2-chloroethane in place of 1-bromo-3-chloropropane. Analysis Calc'd for $C_{22}H_{29}N_3O$ 3HCl; C, 7.16; H, 55.18; N, 8.77. Found: C, 7.13; H, 55.56; N, 8.8.

EXAMPLE 12

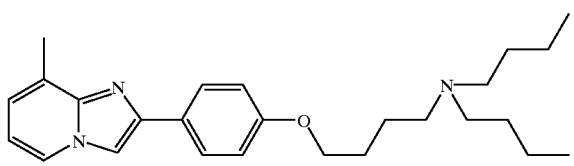

2-(4-Dibutylaminobutoxyphenyl)-8-methylimidazo [1,2-a]pyridine $K_i$=1000 nM

The title compound was prepared by condensing di-butylamine with 2-(4-chlorobutoxyphenyl)-8-methylimidazo[1,2-a]pyridine. 2-(4-Chloroethoxyphenyl)-8-methylimidazo[1,2-1]pyridine was prepared according to the procedure described in Example 1 above using 1-bromo-4-chlorobutane in place of 1-bromo-3-chloropropane. Analysis Calc'd for $C_{26}H_{37}N_3O$ 3HCl; C, 7.91; H, 58.37; N, 7.85. Found: C, 8.2; H, 58.25; N, 7.77.

EXAMPLE 13

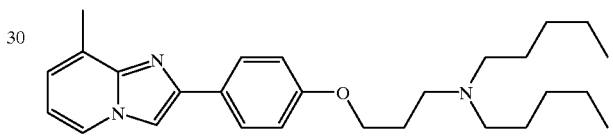

2-(4-Dipentylaminopropoxyphenyl)-8-methylimidazo[1,2-a]pyridine $K_i$=500 nM

This compound was prepared according to the procedure described in Example 1 above using 2-(4-chloropropoxyphenyl)-8-methylimidazo[1,2-a]pyridine and dipentylamine instead of 2-(4-chloropropoxyphenyl)-imidazo[1,2-a]pyridine and dibutylamine respectively. Analysis Calc'd for $C_{27}H_{39}N_3O$3HCl; C, 8.03; H, 60.05; N, 7.78. Found: C, 8.35; H, 60.16; N, 7.39.

EXAMPLE 14

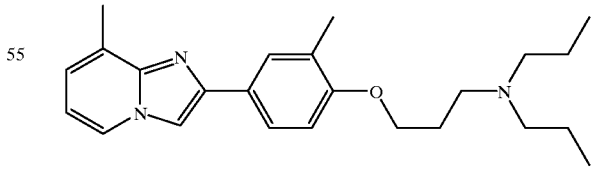

2-(4-Dipropylaminopropoxy-(3-methyl)-phenyl)-8-methylimidazo[1,2-a]pyridine $K_i$=14 nM Step A Preparation of alpha-bromo-4-hydroxy-3-methylacetophenone A mixture of 4-hydroxy-3-methylacetophenone (10 g) in ether (300 mL) was treated with bromine (3.4 mL) and the mixture stirred for 18 hours. The mixture was poured into saturated sodium bicarbonate solution (500 mL) and the organic layer was separated. The aqueous layer was washed with a fresh portion of ether, and the combined organic layers were washed with brine, dried over sodium sulfate, filtered, and evaporated to yield the title compound (16.2 g).

Step B Preparation of 2-(4-hydroxy-3-methylphenyl)-8-methylimidazo[1,2-a]pyridine A solution of the product of Step A (15.0 g) and 2-amino-3-picoline (7.1 mL) in ethanol (200 mL) was heated at reflux temperature for 4 hours. The reaction mixture was cooled to ambient temperature and filtered. The residue was crystallized from ethanol to give the title compound (15.1 g).

Step C Preparation of 2-(4-chloropropoxy-3-methylphenyl)-8-methylimidazo[1,2-a]pyridine The product of Step B (6.0 g) in N, N-dimethylformamide (200 mL) was added to a suspension of 60% sodium hydride (2.0 g) in N, N-dimethylformamide (200 mL). The mixture was stirred at ambient temperature for 1 hour and then treated with 1-bromo-3-chloropropane (30 mL). The mixture was stirred at ambient temperature for 18 hours and partitioned between ethyl acetate and water. The organic portion was washed with water, dried over sodium sulfate, filtered and evaporated to give the title compound (6.2 g).

Step D Preparation of 2-(4-dipropylaminopropoxy-(3-methyl)-phenyl)-8-methylimidazo[1,2-a]pyridine The product of Step C (3.0 g) and dibutylamine (10.0 mL) were heated at reflux temperature for 18 hours. The reaction was evaporated and the residue was purified via silica gel chromatography (dichloromethane/methanol) to give the title compound.

EXAMPLE 15

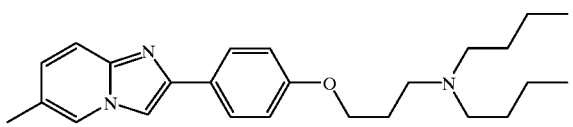

2-(4-Dibutylaminopropoxyphenyl)-6-methylimidazo[1,2-a]pyridine $K_i$=1000 nM

Step A Preparation of p-chloropropoxyacetophenone

A mixture of p-hydroxyacetophenone (106 g) and 1-bromo-3-chloropropane (309 mL) in methanol (800 mL) was treated with potassium hydroxide (65.5 g). The mixture was stirred at reflux temperature for 2 hours when an additional portion of potassium hydroxide (65.5 g) was added and the resulting mixture maintained at reflux temperature for 16 hours. The reaction was cooled to ambient temperature and filtered. The filtrate was concentrated in vacuo and unreacted 1-bromo-3-chloropropane removed ia distillation. The residue was dissolved in ether (500 mL), washed with water (500 mL), dried over magnesium sulfate, filtered and evaporated to yield the title compound (147 g).

Step B Preparation of alpha-bromo-4-chloropropoxyacetophenone

A solution of the product of Step A (147 g) in ether (500 mL) was treated with bromine (110 g) and the mixture stirred at ambient temperature for 10 minutes. The mixture was poured into saturated sodium bicarbonate solution (500 mL) and the organic layer was separated. The organic layer was washed with a fresh portion of saturated sodium bicarbonate solution (500 mL), dried over magnesium sulfate, filtered, and evaporated to yield the title compound (119 g).

Step C Preparation of 2-(4-chloropropoxyphenyl)-6-methylimidazo[1,2-a]pyridine

A solution of the product of Step B (6.3 g) and 2-amino-5-picoline (17 g) in acetone (150 mL) was heated at reflux temperature for 2 hours. The reaction mixture was cooled to ambient temperature and filtered to afford the title compound (8.6 g).

Step D Preparation of 2-(4-dibutylaminopropoxyphenyl)-6-methylimidazo[1,2-a]pyridine The product of Step C (8.6 g) and dibutylamine (9 mL) were heated at reflux temperature for 8 hours. The reaction was cooled to ambient temperature and evaporated in vacuo. The residue was purified via silica gel chromatography (dichloromethane/acetone) to give the title compound which was converted to a hydrochloride salt upon addition of concentrated hydrochloric acid. The salt was recrystallized (methanol/acetone/ether) to give 5.66 g of product. (m.p. 188–191° C).

F. Biological Examples

In the present invention receptor binding was determined using the human histamine $H_3$ receptor (See Lovenberg et al Mol. Pharmacol. 1999, 1107). Screening using the human receptor is particularly important for the identification of new therapies for the treatment of human disease. Conventional binding assays for example are determined using rat synaptosomes (Garbarg et al J. Pharmacol. Exp. Ther. 1992, 263, 304), rat cortical membranes (West et al Mol. Pharmacol. 1990, 610), and guinea pig brain (Korte et al Biochem. Biophys. Res. Commun. 1990, 978). Only limited studies have been performed previously using human tissue but these allude to significant differences in the pharmacology of rodent and primate receptors (West et al Eur. J. Pharmacol. 1999, 233).

Biological Example 1

1(A) Transfection of Cells with Human Histamine Receptor

A 10 cm tissue culture dish with a confluent monolayer of SK-N-MC cells was split two days prior to transfection. Using sterile technique the media was removed and the cells were detached from the dish by the addition of trypsin. One fifth of the cells were then placed onto a new 10 cm dish. Cells were grown in a 37° C. incubator with 5% $CO_2$ in Minimal Essential Media Eagle with 10% Fetal Bovine Serum. After two days cells were approximately 80% confluent. These were removed from the dish with trypsin and pelleted in a clinical centrifuge. The pellet was then re-suspended in 400 μL complete media and transferred to an electroporation cuvette with a 0.4 cm gap between the electrodes (Bio-Rad #165-2088). One microgram supercoiled $H_3$ receptor cDNA was added to the cells and mixed. The voltage for the electroporation was set at 0.25 kV, the capacitance is set at 960 μF.

After electroporation the cells were diluted into 10 mL complete media and plated onto four 10 cm dishes. Due to the variability in the efficiency of electroporation, four different concentrations of cells were plated. The ratios used were: 1:20, 1:10, and 1:5, with the remainder of the cells being added to the fourth dish. The cells were allowed to recover for 24 hours before adding the selection media (complete media with 600 μg/ml G418). After 10 days dishes were analyzed for surviving colonies of cells. Dishes with well-isolated colonies were used. Cells from individual colonies were isolated and tested. SK-N-MC cells were used because they give efficient coupling for inhibition of adenylate cyclase. The clones that gave the most robust inhibition of adenylate cyclase in response to histamine were used for further study.

1(B) [$^3$H]-N-methylhistamine Binding

Cell pellets from histamine H$_3$ receptor-expressing SK-N-MC cells were homogenized in 20 mM TrisHCl/0.5 mM EDTA. Supernatants from a 800 g spin were collected, recentrifuged at 30,000 g for 30 minutes. Pellets were rehomogenized in 50 mM Tris/5 mM EDTA (pH 7.4). Membranes were incubated with 0.8 nM [$^3$H]-N-methylhistamine plus/minus test compounds for 45 minutes at 25° C. and harvested by rapid filtration over GF/C glass fiber filters (pretreated with 0.3% polyethylenimine) followed by four washes with ice cold buffer. Filters were dried, added to 4 mL scintillation cocktail and then counted on a liquid scintillation counter. Non-specific binding was defined with 10 µM histamine according to Chen and Prusoff, *Biochem. Pharmacol.* 1973, 22:3099. K$_I$ values were calculated based on a K$_D$ of 800 pM and a ligand concentration ([L]) of 800 pM according to the formula: K$_I$=(IC$_{50}$)/(1+([L]/(K$_D$)). K$_I$ values are provided in the examples above.

F. Other Embodiments

The features and advantages of the invention are apparent to one of ordinary skill in the art. Based on this disclosure, including the summary, detailed description, background, examples, and claims, one of ordinary skill in the art will be able to make modifications and adaptations to various conditions and usages. These other embodiments are also within the scope of the invention.

What is claimed is:

1. A method for treating disorders mediated by the histamine H$_3$ receptor in a patient, said method comprising administering to the patient a pharmaceutically effective amount of compound of formula (I):

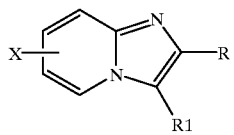

(I)

wherein
X is H or one or more of halogen, hydroxy, C$_{1-3}$ alkoxy, benzyloxy, or C$_{1-6}$ alkyl;
R is H or Ar;
R$_1$ is H, methyl, or Ar;
Ar is —(C=O)$_n$—Ph—O—(CH$_2$)$_m$—N(R$_2$)$_2$;
R$_2$ is C$_{1-6}$ alkyl;
n is 0 or 1 when R is Ar or 1 when R$_1$ is Ar;
m is 2–6;
at least one of R and R$_1$ is Ar; and both of R and R$_1$ are not Ar;
or a pharmaceutically acceptable salt, ester, or amide thereof.

2. A method of claim 1, wherein said compound is a histamine H$_3$ receptor antagonist.

3. A method of claim 1, wherein said compound has a formula wherein each X is independently selected from H, methyl, fluoro, chloro, bromo, and hydroxy.

4. A method of claim 3, wherein each X is H, methyl, or fluoro.

5. A method of claim 1, wherein said compound has a formula wherein R is Ar.

6. A method of claim 1, wherein said compound has a formula wherein R$_1$ is H or methyl.

7. A method of claim 1, wherein each R$_2$ is independently selected from methyl, ethyl, propyl, isopropyl, butyl, and pentyl.

8. A method of claim 7, wherein each R$_2$ is propyl, isopropyl, or butyl.

9. A method of claim 1, wherein m is 2, 3, or 4.

10. A method of claim 9, wherein m is 3.

11. A method of claim 1, wherein n is 0.

12. A method of claim 1, wherein n is 1.

13. A method of claim 1, wherein X is H or methyl; R is Ar; R$_1$ is H or methyl; m is 2, 3, or 4; n is 0.

14. A method of claim 1, wherein said compound is selected from:
2-(4-Dibutylaminopropoxyphenyl)imidazo[1,2-a]pyridine; 2-(4-Dibutylaminopropoxyphenyl)-8-methylimidazo[1,2-a]pyridine; 3-(4-Dibutylaminopropoxybenzoyl)-8-methylimidazo[1,2-a]pyridine; 2-(4-Dibutylaminopropoxyphenyl)-3,8-dimethylimidazo[1,2-a]pyridine; 2-(4-Dibutylaminopropoxybenzoyl)-8-methylimidazo[1,2-a]pyridine; 3-(4-Dibutylaminopropoxybenzoyl)-6-bromoimidazo[1,2-a]pyridine; 2-(4-Dipropylaminopropoxyphenyl)-8-methylimidazo[1,2-a]; 2-(4-Dimethylaminopropoxyphenyl)-8-methylimidazo[1,2-a]; 2-(4-Dimethylaminopropoxyphenyl)imidazo[1,2-a]pyridine; 2-(4-Diethylaminoethoxyphenyl)-8-methylimidazo[1,2-a]pyridine; 2-(4-Diisopropylaminoethoxyphenyl)-8-methylimidazo[1,2-a]pyridine; 2-(4-Dibutylaminobutoxyphenyl)-8-methylimidazo[1,2-a]pyridine; 2-(4-Dipentylaminopropoxyphenyl)-8-methylimidazo[1,2-a]pyridine; 2-(4-Dipropylaminopropoxy-(3-methyl)-phenyl)-8-methylimidazo[1,2-a]pyridine; and 2-(4-Dibutylaminopropoxyphenyl)-6-methylimidazo[1,2-a]pyridine.

15. A method of claim 1, wherein said compound is selected from 2-(4-dibutylaminopropoxyphenyl)imidazo[1,2-a]pyridine; 2-(4-dibutylaminopropoxyphenyl)-8-methylimidazo[1,2-a]pyridine; 2-(4-dibutylaminopropoxyphenyl)-6-bromoimidazo[1,2-a]-pyridine; 2-(4-dibutylaminopropoxyphenyl)-7-methylimidazo-[1,2-a]pyridine; 2-(4-dibutylaminopropoxyphenyl)-3,8-dimethyl imidazo[1,2-a]pyridine; 2-(4-dibutylaminopropoxyphenyl)-8-hydroxyimidazo[1,2-a]pyridine; and 2-(4-dibutylaminopropoxyphenyl)-8-benzyloxyimidazo[1,2-a]pyridine.

16. A method of claim 1, wherein said compound is selected from 2-(4-dibutylaminopropoxybenzoyl)-8-methylimidazo[1,2-a]-pyridine; 2-(4-dibutylaminopropoxybenzoyl)-5,7-dimethylimidazo[1,2-a]pyridine; 2-(4-dibutylaminopropoxybenzoyl)-7-methylimidazo[1,2-a]pyridine; 2-(4-dibutylaminopropoxybenzoyl)-8-benzyloxyimidazo[1,2-a]pyridine; and 2-(4-dibutylaminopropoxybenzoyl)-6-bromoimidazo[1,2-a]pyridine.

17. A method of claim 1, wherein said compound is selected from 3-(4-dibutylaminopropoxybenzoyl)-8-methylimidazo[1,2-a]-pyridine and 3-(4-dibutylaminopropoxybenzoyl)-6-bromoimidazo[1,2-a]pyridine.

18. A method for treating a patient with a central nervous system disorder, said method comprising administering to the patient a pharmaceutically-effective amount of a compound of formula (I).

19. A method of claim 18, wherein said compound has a formula wherein X is H or methyl; R is Ar; $R_1$ is H or methyl; m is 2, 3, or 4; and n is 0.

20. A method of claim 18, wherein said compound is selected from:

2-(4-Dibutylaminopropoxyphenyl)imidazo[1,2-a]pyridine; 2-(4-Dibutylaminopropoxyphenyl)-8-methylimidazo[1,2-a]pyridine; 3-(4-Dibutylaminopropoxybenzoyl)-8-methylimidazo[1,2-a]pyridine; 2-(4-Dibutylaminopropoxyphenyl)-3,8-dimethylimidazo[1,2-a]pyridine; 2-(4-Dibutylaminopropoxybenzoyl)-8-methylimidazo[1,2-a]pyridine; 3-(4-Dibutylaminopropoxybenzoyl)-6-bromoimidazo[1,2-a]pyridine; 2-(4-Dipropylaminopropoxyphenyl)-8-methylimidazo[1,2-a]; 2-(4-Dimethylaminopropoxyphenyl)-8-methylimidazo[1,2-a]; 2-(4-Dimethylaminopropoxyphenyl)imidazo[1,2-a]pyridine; 2-(4-Diethylaminoethoxyphenyl)-8-methylimidazo[1,2-a]pyridine; 2-(4-Diisopropylaminoethoxyphenyl)-8-methylimidazo[1,2-a]pyridine; 2-(4-Dibutylaminobutoxyphenyl)-8-methylimidazo[1,2-a]pyridine; 2-(4-Dipentylaminopropoxyphenyl)-8-methylimidazo[1,2-a]pyridine; 2-(4-Dipropylaminopropoxy-(3-methyl)-phenyl)-8-methylimidazo[1,2-a]pyridine; and 2-(4-Dibutylaminopropoxyphenyl)-6-methylimidazo[1,2-a]pyridine.

21. A method of claim 18, wherein said central nervous system disorder is selected from sleep/wake disorders, arousal/vigilance disorders, dementia, Alzheimer's disease, epilepsy, narcolepsy, eating disorders, motion sickness, vertigo, attention deficit hyperactivity disorder, learning and memory disorders, sequelae associated with post-ischemic reperfusion, and schizophrenia.

22. A method of claim 18, wherein said central nervous system disorder is selected from Alzheimer's disease, epilepsy, eating disorders, learning and memory disorders, migraine, sleep/wake disorders, allergic rhinitis, schizophrenia, mild cognitive impairment, and asthma.

23. A method of claim 18, wherein said disorder is selected from sleep/wake disorders, arousal/vigilance disorders, mild cognitive impairment, attention deficit hyperactivity disorder, and learning and memory disorders.

24. A method for treating a patient with an upper airway allergic response, said method comprising administering to the patient a pharmaceutically-effective amount of a compound of formula (I).

25. A method of claim 24, wherein said compound has a formula wherein X is H or methyl; R is Ar; $R_1$ is H or methyl; m is 2, 3, or 4; and n is 0.

26. A method of claim 24, wherein said compound is selected from:

2-(4-Dibutylaminopropoxyphenyl)imidazo[1,2-a]pyridine; 2-(4-Dibutylaminopropoxyphenyl)-8-methylimidazo[1,2-a]pyridine; 3-(4-Dibutylaminopropoxybenzoyl)-8-methylimidazo[1,2-a]pyridine; 2-(4-Dibutylaminopropoxyphenyl)-3,8-dimethylimidazo[1,2-a]pyridine; 2-(4-Dibutylaminopropoxybenzoyl)-8-methylimidazo[1,2-a]pyridine; 3-(4-Dibutylaminopropoxybenzoyl)-6-bromoimidazo[1,2-a]pyridine; 2-(4-Dipropylaminopropoxyphenyl)-8-methylimidazo[1,2-a]; 2-(4-Dimethylaminopropoxyphenyl)-8-methylimidazo[1,2-a]; 2-(4-Dimethylaminopropoxyphenyl)imidazo[1,2-a]pyridine; 2-(4-Diethylaminoethoxyphenyl)-8-methylimidazo[1,2-a]pyridine; 2-(4-Diisopropylaminoethoxyphenyl)-8-methylimidazo[1,2-a]pyridine; 2-(4-Dibutylaminobutoxyphenyl)-8-methylimidazo[1,2-a]pyridine; 2-(4-Dipentylaminopropoxyphenyl)-8-methylimidazo[1,2-a]pyridine; 2-(4-Dipropylaminopropoxy-(3-methyl)phenyl)-8-methylimidazo[1,2-a]pyridine; and 2-(4-Dibutylaminopropoxyphenyl)-6-methylimidazo[1,2-a]pyridine.

\* \* \* \* \*